United States Patent
Zeng

(10) Patent No.: US 6,964,949 B2
(45) Date of Patent: *Nov. 15, 2005

(54) PHARMACEUTICAL COMPOSITIONS FOR PROMOTING THE GROWTH OF GRAM-POSITIVE BACILLI AND INCREASING THE ACIDITY IN THE VAGINA AND THE USE THEREOF

(75) Inventor: Zhongming Zeng, Shenzhen (CN)

(73) Assignee: Shanghai Jiao Da Onlly Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 10/643,003

(22) Filed: Aug. 18, 2003

(65) Prior Publication Data

US 2004/0110721 A1 Jun. 10, 2004

Related U.S. Application Data

(63) Continuation-in-part of application No. 09/577,858, filed on May 24, 2000, now Pat. No. 6,632,796.

(51) Int. Cl.[7] .............................................. A61K 31/70
(52) U.S. Cl. ........................................ 514/23; 514/53
(58) Field of Search ..................................... 514/23, 53

(56) References Cited

U.S. PATENT DOCUMENTS

| | | | |
|---|---|---|---|
| 3,860,707 A | | 1/1975 | Wootton |
| 5,518,733 A | | 5/1996 | Lamothe et al. |
| 6,165,997 A | * | 12/2000 | Cohen et al. ............... 514/148 |
| 6,416,779 B1 | * | 7/2002 | D'Augustine et al. ...... 424/430 |
| 6,632,796 B1 | * | 10/2003 | Zeng ........................... 514/23 |

FOREIGN PATENT DOCUMENTS

| | | |
|---|---|---|
| CN | 1104502 A | 5/1995 |
| CN | 1104502 | 7/1995 |
| EP | 0 257 007 A1 | 2/1988 |
| EP | 0 242 459 B1 | 8/1991 |
| GB | 2 112 285 A | 7/1983 |
| WO | WO-89/05645 A1 | 6/1989 |
| WO | WO-93/14773 A1 | 8/1993 |
| WO | WO 94/02148 | 2/1994 |
| WO | WO 94/03502 | 2/1994 |

OTHER PUBLICATIONS

McDonald, H.M., et al.; "Vaginal Infection and Preterm Labour"; *Br. J. Obstet Gynaecol*; vol. 98, No. 5; pp. 427–435 (May 1991).

Thomason, Jessica L.; "Bacterial Vaginosis: Current Review With Indications for Asymptomatic Therapy";Am. *J. Obstet Gynecol*; vol. 165; No. 4, Part 2; pp. 1210–1217 (1991).

Hillier, Sharon, L.; "Efficacy of Intravaginal 0.75% Metronidazole Gel for the Treatment of Bacterial Vaginoisis"; *Obstet–Gynecol*.; vol. 81, No. 6; pp. 963–967 (Jun. 1993).

Hallén, Anders, Md., et al.; "Treatment of Bacterial Vaginois With Lactobacilli"; *Sex–Transm–Dis*.; vol. 19, No. 3; pp. 146–148 (May–Jun. 1992).

Hughes, Viki, L.; "Microbiologic Characteristics of Lactobacillus Products Used for Colonization of the Vagina"; *Obstetrics & Gynecology*; vol. 75, No. 2; pp. 244–248 (Feb. 1990).

Eschenbach, David, A.; "Bacterial Vaginosis and Anaerobes in Obstetric–Gynecologic Infection", *Clinical Infectious Diseases*; vol. 16; Supp. 4; pp. S282–S287 (1993).

Germain, Marc, et al., "Genital Flora in Pregnancy and Its Association With Intrauterine Growth Retardation"; *J. Clin. Microbiol*; vol. 32, No. 9; pp. 2162–2168 (Sep. 1994).

M.R. Guiraud, "Le Traitement Des Vulvo–Vaginites", Bourdeaux Medical, France, vol. 11, No. 16, Jun. 1978, pp. 1393–1400.

B. Kaplan, et al., "Single–dose systemic oral fluconazole for the treatment of vaginal cadidiasis", International Journal of Gynecology & Obstetrics, vol. 57, No. 3, 1997, pp. 281–286.

* cited by examiner

*Primary Examiner*—Elli Peselev
(74) *Attorney, Agent, or Firm*—Darby & Darby

(57) ABSTRACT

The present invention relates to a pharmaceutical formulation for stimulating the growth of gram-positive bacilli and increasing the acidity in the vagina which comprises sucrose and/to maltose, to the use of certain sucrose and/or maltose, in preparing the pharmaceutical formulation for stimulating the growth of gram-positive bacilli and increasing the acidity in the vagina, in particular to a method of stimulating the growth of gram-positive bacilli and increasing the acidity in the vagina, treating the reduction of gram-positive bacilli and the lowness of acidity in vagina as well as the vaginitis and the disturbance of vaginal bacterioflora accompanying the reduction of gram-positive bacilli, especially bacterial vaginal disease.

19 Claims, No Drawings

PHARMACEUTICAL COMPOSITIONS FOR PROMOTING THE GROWTH OF GRAM-POSITIVE BACILLI AND INCREASING THE ACIDITY IN THE VAGINA AND THE USE THEREOF

This application is a continuation-in-part application of Ser. No. 09/577,858, now U.S. Pat. No. 6,632,796 which is hereby incorporated by reference in its entirety.

FIELD OF THE INVENTION

This invention relates to pharmaceutical compositions containing saccharides as active ingredients for promoting the growth of Gram-positive bacilli and increasing the acidity in the vagina, to the use of particular saccharides in the preparation of compositions for promoting the growth of Gram-positive bacilli and increasing the acidity in the vagina, and especially to a method of promoting the growth of Gram-positive bacilli and increasing the acidity in the vagina, treating decreased levels of Gram-positive bacilli and decreased levels of acidity in the vagina, treating vaginitis and disturbances of the vaginal bacterial flora accompanying the reduction of Gram-positive bacilli, especially bacterial vaginosis.

BACKGROUND OF THE INVENTION

High acidity in female vagina is one important anti-infective mechanism of the vagina and is of great significance for vaginal health. Lactobacilli and other Gram-positive bacilli that can produce and resist acids serve an important role in maintaining the normal acidity in the vagina by keeping the vaginal pH value in the range from 4.0 to 4.6. They are the physiological bacterial flora of vagina, whereas Gram-negative bacilli, Gram-negative cocci, and Gram-positive cocci are relatively less abundant in the healthy vagina.

When the Gram-positive bacilli are reduced or disappear in vagina, vaginal pH value rises and disturbance of vaginal bacterial flora results from abnormal increases of Gram-negative bacilli, Gram-negative cocci and Gram-negative cocci, which can cause harm to the human body and lead to a range of diseases. The most typical condition resulting from altered vaginal flora is bacterial vaginosis (BV). BV is characterized by the reduction or even disappearance of Lactobacillus and other Gram-positive bacilli in the vagina, accompanied by decreased acidity (pH value>4.6) in the vagina, and abnormal increases of such bacteria as Gram-negative bacilli including Gardnerella, Bacteroides and motile-curved bacilli; Gram-negative cocci such as Veillonella; and Gram-positive cocci such as Streptococcus. Such changes in the bacterial flora can cause vaginal secretions to exhibit an unpleasant odor, and may be associated with pruritus of vulva, and symptoms. In addition, BV may also be related to IUGR [1], PTL, PROM [2], abortion, and obstetric infections such as chorio-amnionitis, puerperal endometritis, vaginal wall phlegmon after hysterectomy, female upper genital tract infection (salpingitis), and urinary infection, etc. [3]. A high rate of morbidity is associated with vaginal bacterial flora disturbance. According to one report, about 45% or more vaginitis cases result from disturbance of vaginal bacterial flora [3], and 4–15% of American female students in universities suffer from bacterial vaginosis [4], which has led to serious compromise to health and quality of life.

There are few options for treatment of reduced Gram-positive bacilli colonization, decreased vaginal acidity, and related disturbances of vaginal bacterial flora, vaginitis, and bacterial vaginosis. Therapeutic options currently include:

1) Antibacterial drugs which are used to suppress the growth of Gram-negative bacilli and other abnormal bacteria. These most commonly include clindamycin and metronidazole [5–6]. These drugs suppress the bacteria that are abnormally increased in the vagina but may also affect the Gram-positive bacilli. After administration of these drugs, the Gram-positive bacilli (lactobacilli) can not be restored very well, and it is very difficult to lower the pH value in the vagina to normal level.

2) Lactic acid-containing pharmaceutical compositions. Vaginal secretions from patients suffering from bacterial vaginosis have elevated pH values. Swedish researchers used lactic acid gel for the improvement and recovery of the low-acidity conditions in vagina, and reported that this treatment can restore the Gram-positive bacilli (lactobacilli) in the vaginas of some of the patients [7]. But the study also showed that the lactic acid pharmaceutical preparation is less effective than the antibacterial drugs [8].

3) Lactobacillus preparations. Most of the Gram-positive bacilli in vagina are lactobacillus. If there is disturbance of vaginal bacterial flora, the lactobacilli will be reduced or disappear, and Gram-negative bacilli, Gram-negative, and Gram-positive cocci, will increase. The Gram-positive bacilli in the vagina of some patients can be restored by directly adding lactobacilli in the vagina [9]. However, stable colonization is generally not achieved. Moreover, it is difficult to maintain viability of the lactobacillus preparations during storage, with viable counts in such preparations decreasing during storage, compromising their useful shelf life [10].

The international Patent Application WO94/02148 discloses a pharmaceutical composition for treating vulvitis and vulvovaginitis, and indicates that such compositions can promote restoration of vaginal epithelium tissues while alleviating the symptoms. Its preferred composition comprises 7 to 8 active substances. Some preferred compositions may contain 3.0–15.0% (by weight/volume) lactose or glucose. As mentioned in page 5 lines 8–10 of the published specification, the lactose or glucose contained in these compositions is used as carbon source. But this application does not mention that saccharides can be used solely as the effective component for treating vulvitis and vulvovaginitis, and nor does it disclose explicitly or implicitly that the disclosed compositions can stimulate the growth of Gram-positive bacilli in vagina. Furthermore, it does not indicate that any other kinds of sugar can be used as active components of a composition for treating related vaginal diseases. Besides, as mentioned in page 5 lines 17–18 of the specification, this application emphasizes that it is important for the pH value of the compositions be between 2 and 3.5.

The U.S. Pat. No. 3,860,707 teaches a method for treating trichomonal vaginitis and monilial vaginitis. This method comprises administering lactulose into the vagina. This patent also indicates that lactulose can be administered after being mixed with some carriers such as glucose, lactose and galactose, wherein lactulose is required to have a concentration as high as 50%, and the mixture also contains 5% lactose, 8% galactose as carriers, as mentioned in column 1 lines 51–55 and column 5 lines 1–5 of the patent specification. The quantity of lactulose is 4–10 grams administered with each dose, which is taken once or twice daily, as shown in Column 4 Lines 63–66 of the specification. But this patent does not describe the treatment effectiveness on bacterial vaginosis or other vaginal diseases different from monilial vaginitis, nor does it suggest that the lactulose of low or medium concentration (2.5–17%) and small dosage (daily total amount 0.24–2.1 grams) would be able to stimulate the growth of Gram-positive bacillus and increase the acidity of the vagina. Furthermore, it fails to indicate whether any saccharide other than lactulose has treatment effects.

European Patent Application EP-A-0257007 discloses a pharmaceutical composition containing lactic acid and buffering substances and substrate to support growth of lactobacillus, which can be used to improve microenvironment in vagina and suppress the growth of harmful bacteria in the vagina, so as to facilitate the growth of lactobacilli. This patent application discloses that glycogen or lactose can be used as the said substrate. But as mentioned in Column 6 Line 10–14 of the specification, the main ingredient of this composition is lactic acid. The lactic acid and the glycogen and/or lactose are incorporated in a ratio by weight of from 20:1 down to 500:1, and the content of glycogen and/or lactose is only 0.1–0.166% (W/V). It also stresses that the pH value of the pharmaceutical composition should be adjusted to 3.5 to 4.0, which is very important. The in vitro experimental results disclosed in this application show that this composition can effectively and selectively kill pathogenic bacteria, and lactobacilli can survive in this composition for a longer time than the pathogenic microorganisms. But no test in vitro or vivo shows that this composition can stimulate the growth of lactobacilli or produce acids. Nor does this application mention the treatment effect of glycogen or lactose or any other saccharides when they are used separately as active ingredients.

GB21 12285A discloses a lotion composition for cleaning the vagina. It is a buffering liquid comprising acetic acid or lactic acid plus sodium acetate with a pH value of 5.71 to 6.2 as shown in the examples. It also contains nutrients to support the growth of lactobacillus [1–2% (W/V) glucose and unsaturated fatty acid]. It also generally mentions inclusion of mono- and/or disaccharides. The main therapeutic mechanism of this composition is that the buffering lotion comprising acetic acid or lactic acid plus sodium acetate can selectively suppress pathogens and not suppress lactobacilli. As shown in claims 2 and 3 and the in vitro test data of this application, this lotion can effectively suppress many kinds of pathogens, and lactobacilli survive in this composition for a longer time. No data from test in vitro or vivo indicates that this lotion has an activity of promoting the growth of lactobacilli and producing acid, nor does it indicate the treatment effect of glucose or any other sugar when used separately as active ingredients. This application teaches that lactobacilli regulate pH value in vagina to about 5.8, as shown in Page 1 Lines 20–23 of the specification, which is strongly contradicted by most knowledgeable investigators.

The above-mentioned pharmaceutical compositions disclosed in patent applications EP-A-0257007 and GB2112285A which contain lactic acid, acetic acid and other selective inhibitors as main active ingredients have strong suppressive action on pathogens but no explicit suppressive action on lactobacilli, although they may indirectly facilitate the growth of vaginal lactobacilli. These compositions themselves, however, cannot directly promote significant growth of lactobacilli, and only regulate vaginal acidity for a short time. Therefore, it remains very difficult to restore the physiological conditions dominated by the Gram-positive bacillus-flora and to restore the vaginal acidity to its normal value.

The object of the present invention is to provide a composition for promoting the growth of Gram-positive bacilli and the production of acids, and thus increase the acidity in the vagina. Another object of the present invention is to provide a method by using such composition for reversing the reduction of Gram-positive bacilli, lack of vaginal acidity and treating related vaginal diseases.

In order to seek a composition which is effective in promoting the growth of Gram-positive bacilli, producing acid, and enhancing the acidity in the vagina, the inventor has conducted an extensive study, performed tests by using various pharmaceutical compositions known in the prior art, and has not found any compositions promoting the growth of Gram-positive bacilli among the existing compositions. After repeated tests and intensive study, the inventor has found very surprisingly that sucrose and maltose both have a strong effect in promoting the growth of Gram-positive bacilli and producing acids if they are presented in a concentration and at a pH value in specific ranges. Combined in vitro culturing experiments show that the two saccharides can stimulate the growth of Gram-positive bacilli, increasing their numbers significantly. To our surprise, although pH values above 4.6 in vagina are considered un-physiologic, and most of state-of-the-art technologies stress that the pharmaceutical compositions used in vagina must have a pH value equal to 4.0 or below, the inventor has discovered that, if they have pH value between 4.1 and 7.2, and especially above pH 5.0, sucrose and maltose can stimulate the growth of Gram-positive bacilli of women vagina and the production of acid, and are able to decrease the pH value in vagina to less than 4.6. However, if they have pH values of 4.0 or less, they do not exert significant growth-promoting effects on Gram-positive bacilli nor upon acid production and the pH of the vagina can rarely be reduced to below 4.6. Based on the above discoveries and further study, the inventor has completed the present invention.

SUMMARY OF THE INVENTION

The present invention provides a water-based pharmaceutical composition for promoting the growth of Gram-positive bacilli and increasing the acidity in the vagina comprising, based on the volume of the composition, 2.5% to 17% (W/V) of sucrose and/or maltose and optionally one or more saccharides selected from the group consisted of glucose, fructose, galactose, mannose, lactose, lactulose, mycose, cellobiose, melibiose, melitose, malto-oligosaccharide, iso-malto-oligosaccharide and oligo-fructose, dextrim, starch and glycogen, at pH-value of 4.1–7.2 adjusted with pharmaceutically acceptable acid or alkali, optionally a pharmaceutically acceptable viscous base, and optionally an effective amount of anti-fungal and/or an anti-bacterial agents.

The invention also provides a use of sucrose and/or maltose as active ingredient in the preparation of pharmaceutical compositions for promoting the growth of Gram-positive bacilli and increasing the acidity in the vagina.

The invention also relates to a method for promoting the growth of Gram-positive bacilli and increasing the acidity in the vagina, comprising administering to the subject in need of such treatment a therapeutically effective amount of the pharmaceutical composition according to the present invention.

The present application further relates to a composition for treating a patient suffering from vaginitis, a disturbance of the vaginal bacterial flora or bacterial vaginosis, wherein said vaginitis, disturbance of the vaginal bacterial flora or bacterial vaginosis are accompanied with a reduction of the number of Gram-positive bacilli, said composition comprising:

(a) Sucrose and/or maltose in a concentration of from about 2.5% to about 17% w/v based on the total volume of the composition,
(b) An anti-fungal drug in a concentration of from about 0.0001% to about 5% w/v based on the total volume of the composition, and
(c) A sufficient amount of a pharmaceutically acceptable acid or alkali, which results in a pH of the composition from about 4.1 to about 7.2.

The above-mentioned pharmaceutical composition, use and method of treatment according to the invention are useful for the reversal of the reduced numbers of vaginal Gram-positive bacilli, decreased vaginal acidity, as well as for treating vaginitis and the disturbance of vaginal bacterial flora accompanied with the reduction in numbers of Gram-positive bacilli, especially bacterial vaginosis.

DETAILED DESCRIPTION OF THE INVENTION

As mentioned above, this invention relates to water-based pharmaceutical compositions with pH values between 4.1 and 7.2 intended to promote the growth of Gram-positive bacilli and enhance vaginal acidity, and which contains 2.5–17% (WIV) of one or more of such saccharides as defined above.

The compositions according to the present invention may contain one or a mixture of two or several of such saccharides as defined above. Any hexose used in the invention is of D-type. Starch used in the invention may be amylose or amylopectin. The preferred saccharides are those having low price and abundant sources.

According to this invention, the pharmaceutical composition contains a total content of 2.5–17% (W/V) of saccharides, especially 2.5–16% (W/V), preferably 8–14% (W/V), more preferably 10–13% (W/V), and most preferably 10–12% (W/V). However, the content of the disaccharides other than sucrose and maltose mixed with sucrose and/or maltose must not exceed [(17—content of sucrose and/or maltose) % (W/V)]. The maximum content of hexoses mixed with sucrose and/or maltose should be less than [0.42×(17—disaccharides content) % (W/V)].

The weight/volume content (W/V) mentioned in the context of this application refers to the grams of the specified component in 100 milliliters of the composition.

The compositions formulated according to the preferred contents of saccharides are useful for treating the patients with any vaginal illness states, especially with severe illness (with pH value of vaginal secretion greater than 5.0, and when the vaginal Gram smear proves that there are few or no Gram-positive bacilli). The compositions with a content of saccharides below 8% (W/V) are applicable to the patients suffering from mild diseases (with a vaginal pH value of greater than 4.6, and the vaginal Gram smear proves that there are Gram-positive bacilli, but in which the Gram positive bacilli are fewer in number than the Gram-negative bacilli, Gram-negative cocci, or Gram-positive cocci).

The pH value of the pharmaceutical compositions of this invention is between 4.1 and 7.2, with the optimum pH value between 4.5 and 6.5. The pH value of these compositions can be adjusted by adding any pharmaceutically acceptable acid or alkali, of which the preferred choices are acetic acid, lactic acid, or sodium hydroxide. The nature and concentration of such acid or alkali can be readily determined by a person skilled in the art.

According to this invention, the composition may contain a viscous base. One example of such base is Xanthan Gum with concentration of 1.0–2.2% (W/V), and preferably of 1.4–2.0% (W/V). Xanthan Gum is able to keep the sugar in uniform contact with vaginal mucosa and retain the product within the vaginal vault for a long time due to its high adherence and stability against changes of temperature and pH values, thus permit the compositions to promote the growth of Gram-positive bacilli and increasing the production of acid in vagina.

The composition can also be formulated into hydro-gel form or ointment with other suitable viscous carrier bases, auxiliaries well known to a person skilled in the art.

According to this invention, the composition also may not contain viscous base, it may be administered by means of intravaginal tampon saturated with the liquid composition. The intravaginal tampon may be composed of cotton ball, gauze ball, ribbon gauze, etc. In this embodiment, the composition according to the present invention can also stimulate the growth of Gram-positive bacilli and increase the acidity in the vagina. The preferred use of the composition of this invention does requires that the composition of the invention stay in the vagina for some time before it can stimulate the growth of Gram-positive bacilli and produce vaginal acidity in the vagina. Therefore as a lotion without a viscous base, the composition can not exhibit its therapeutic effect very well.

The saccharide(s) is/are the essential basic active components of the composition of the invention, and can fulfill the object of this invention when used with suitable pharmaceutically acceptable carriers. But these saccharides can produce a better treatment effect if it is combined with minor amount of amino-acid, vitamin or other similar substances, or yeast extract rich in amino-acids and vitamins. The vaginal secretion naturally contains sufficient amino-acids and vitamins. Such amino-acids or vitamins are not available in conventional in vitro experiments and should be added when in vitro experiments are carried out for the composition of the invention.

Sucrose and/or maltose promote the growth of vaginal Gram-positive bacilli and increase vaginal acidity, which would inhibit abnormal vaginal bacterial flora except Gram-positive bacilli. In this way the reduced vaginal Gram-positive bacilli and the disturbance of vaginal flora, vaginitis, or bacterial vaginosis could be cured.

However, the inventor noticed further that in seldom cases Candida coexisted with abnormal vaginal bacterial flora or even BV flora. Although increased vaginal Gram-positive bacilli and vaginal acidity did inhibit abnormal vaginal bacterial flora, it didn't inhibit Candida. Candida might grow better in vagina as a result of inhibition of abnormal vaginal bacterial flora. In order to treat such cases of reduced vaginal Gram-positive bacilli or disturbance of vaginal flora or vaginits or bacterial vaginosis, the inventor conducted further studies and this new composition comprising sucrose and/or maltose and anti-fungi drugs was invented. As the anti-fungi drugs may also be effective against bacteria, the preferred content of anti-fungi drug in this invented composition is in low concentration so to avoid inhibiting Gram-positive bacilli. Compared with some anti-fungi creams available in market whose anti-fungi drugs concentration may be as high as 100 to 1000 times the drug's MIC against Candidal strains, in this invented composition the content of anti-fungi drug may be as low as 0.1~10 times the drug's MIC.

The present application further relates to a composition for treating a patient suffering from vaginitis, a disturbance of the vaginal bacterial flora or bacterial vaginosis, wherein said vaginitis, disturbance of the vaginal bacterial flora or bacterial vaginosis are accompanied with a reduction of the number of Gram-positive bacilli, said composition comprising:

(a) Sucrose and/or maltose in a concentration of from about 2.5% to about 17% w/v based on the total volume of the composition, (b) Anti-fungi drug in a concentration of from about 0.0001% to about 5% w/v based on the total volume of the composition, and (c) A sufficient amount of a pharmaceutically acceptable acid or alkali, which results in a pH of the composition from about 4.1 to about 7.2.

The above mentioned composition may further comprise one or more saccharides from the group consisting of glucose, fructose, galactose, mannose, lactose, lactulose, mycose, cellobiose, melibiose, melitose, malto-oligosaccaride, iso-malto-oligosaccharide and oligo-fructose, dextrin, starch and glycogen.

Preferably, the content of sucrose and/or maltose in said composition is from about 8% to about 14% w/v, the content of anti-fungi drug in said composition is from about 0.001% to about 0.5% w/v. More preferably, the content of anti-fungi drug in said composition is in the range of 0.1 to 10 times of the drug's MIC against Candidal strains.

The anti-fungi drug in the above mentioned composition is selected from the following group: Fluconazole, Terconazole, Tioconazole, Butoconazole, Ketoconazole, Itraconazole, Econazole, Miconazole, and Cannitracin. Preferably, the antifungi drug is selected from Fluconazole, Terconazole, and Tioconazole.

Said composition may be in the form of hydro-gel or ointment, or in the form of liquid for preparing intravaginal tampon. Preferably, the composition is in the form of hydro-gel or ointment, said composition further comprises pharmaceutically acceptable viscous base, preferably, said pharmaceutically acceptable viscous base is Xanthan gum.

The present application also relates to a method for treating a patient suffering from vaginitis, a disturbance of the vaginal bacterial flora or bacterial vaginosis, wherein said vaginitis, disturbance of the vaginal bacterial flora or bacterial vaginosis are accompanied with a reduction of the number of Gram-positive bacilli, said method comprising vaginally administering to a subject in need of such treatment a therapeutically effective amount of a composition comprising:

(a) Sucrose and/or maltose in a concentration of from about 2.5% to about 17% w/v based on the total volume of the composition, (b) Anti-fungi drug in a concentration of from about 0.0001% to about 5% w/v based on the total volume of the composition, and (c) A sufficient amount of a pharmaceutically acceptable acid or alkali, which results in a pH of the composition from about 4.1 to about 7.2;

wherein said administration promotes selective growth of gram-positive bacilli in the vagina of said subject.

The present application further relates to a method for treating a patient suffering from vaginitis, a disturbance of the vaginal bacterial flora or bacterial vaginosis, wherein said vaginitis, disturbance of the vaginal bacterial flora or bacterial vaginosis are accompanied with a reduction of the number of Gram-positive bacilli, said method comprising, simultaneously or sequentially, vaginally administering to a subject in need of such treatment a therapeutically effective amount of a composition (A) and composition (B), Composition (A) comprising:

a) Sucrose and/or maltose in a concentration of from about 2.5% to about 17% w/v based on the total volume of the composition, and b) A sufficient amount of a pharmaceutically acceptable acid or alkali, which results in a pH of the composition from about 4.1 to about 7.2;

Composition (B) comprising:

(a) Anti-fungi drug in a concentration of from about 0.0001% to about 5% w/v based on the total volume of the composition, and (b) A sufficient amount of a pharmaceutically acceptable acid or alkali, which results in a pH of the composition from about 4.1 to about 7.2.

Preferably, composition (A) and composition (B) are vaginally administered to a subject in need of such treatment simultaneously a therapeutically effective amount of a composition (A) and composition (B).

The composition of the invention may also contain one or more anti-bacterial agents that can suppress or kill Gram-negative bacteria but exert no effect or only exert slight effect on Gram-positive bacilli. In this embodiment, the composition of the invention may have an increased efficacy for treating vaginal infection or inflammation. Such anti-bacterial agents may include, but are not limited to polymyxin, metronidazole or aztreonam.

The composition of the invention can be prepared according to the processes known to those skilled in the art.

If the saccharides used include little or no starch, such saccharide should be mixed with viscous auxiliary substances homogeneously, and then distilled water is added into the mixture, which are then stirred to dissolve the saccharide and swell the viscous auxiliary substances until a homogeneous viscous gel is formed. If starch is included, it is sufficient to heat directly the mixture of saccharides and water to form a paste. In the latter case, viscous auxiliary substances may be added or not. For adjusting the pH to a predetermined value, lactic acid or sodium hydroxide solution is added prior to sterilization treatment. Alternatively, sterilization treatment is performed first, followed by adjustment of pH. For sterilization, intermittent sterilization may be used, with the detailed steps described as follows: sterilizing at 80° C. for 30 minutes, keeping at 36° C. for 8–12 hours, sterilizing at 80° C. for 30 minutes, keeping at 36° C. for 8–12 hours and finally sterilizing at 80° C. for 30 minutes. Alternatively, a high-pressure sterilization may be performed for 15–20 minutes at 116° C. A solution of saccharides may also be sterilized by filtering the solution. Then the sterilized saccharide solution may be added to a viscous base in the form of hydro-gel that has been sterilized at high pressure.

The composition of the invention also may be made into a solution by dissolving the saccharides in water. The solution can be administered to a patient by means of an intravaginal tampon soaked in it.

The composition of this invention uses sugar substances as active ingredients, and has good stability during storage, but preferably it is stored under refrigeration or in cool place. The near neutral pH value of the composition is also helpful in stabilizing the sugar components.

The present invention also relates to the use of one or more of such saccharides as defined above as active ingredients in the preparation of a medicament for promoting the growth of Gram-positive bacilli and increasing the acidity in the vagina. This invention uses D-type hexose, either amylose or amylopectin.

The medicament prepared according to the use of the invention can be used for promoting the growth of Gram-positive bacilli and increasing the acidity in the vagina, and reversing decreased numbers of Gram-positive bacilli, diminished vaginal acidity (pH value above 4.6) as well as treating vaginitis and the disturbance of vaginal bacterial flora accompanied with the reduction of Gram-positive bacilli, especially bacterial vaginosis.

The experiments in vitro and in vivo have proven that the composition of the invention can strongly stimulate the growth of Gram-positive bacilli and increase the acidity in the vagina, and can be used for the reversal of the reduction of Gram-positive bacilli, diminished vaginal acidity and treatment of vaginitis and the disturbance of vaginal bacterial flora accompanied with reduction of Gram-positive bacilli, especially bacterial vaginosis.

Therefore, this invention also relates to a method for promoting the growth of Gram-positive bacilli and increasing vaginal acidity, reversing the reduction of Gram-positive bacilli, increasing vaginal acidity and treatment of vaginitis and the disturbance of vaginal bacterial flora that accompanied with reduction of Gram-positive bacilli, especially bacterial vaginosis, wherein the subject in need of such treatment is given a medically-effective amount of the pharmaceutical composition according to the invention.

The administration method of the composition is to administer the composition locally inside the vagina. The composition of the invention containing a tissue viscous base or other carriers may be applied directly to the lumen of the vagina. If the composition of the invention is in the form of a solution, an intravaginal tampon is soaked in the solution, then the tampon is placed inside the vagina.

For the composition and method of treatment according to the invention, the medicament is administered according to the following dosage. For the composition of this invention containing 8–14% (W/V) of saccharides as active ingredients, such composition is applied inside the vagina 1–3 times daily in doses of 1–5 ml, with the total sugar amount controlled to 0.08–2.1 grams daily dosage, generally applied before sleep at night or after arising in the morning, with an additional dose applied at noon for a few patients. For the patients suffering from severely abnormal vaginal bacterial flora and with the pH value of the vaginal secretion greater than 5.0, and if the vaginal Gram smear shows few or no Gram-positive bacilli, more extensive treatment is required with the sugar amount above 0.8 grams daily. For the patients having less severe disease with the pH value of vaginal secretion between 5.0 and 4.6, or if the vaginal Gram smear reveals Gram-positive bacilli, but in lesser abundance than that of any of Gram-negative bacilli, Gram-negative cocci, or Gram-positive cocci, a smaller dosage is used and the total sugar amount is limited to 0.8 grams or less.

During treatment with this composition, clinical symptoms may be observed daily and the vaginal pH value checked for change. Moreover, the vaginal Gram smear may be performed in order to check the change of bacterial flora and adjust the treatment accordingly if necessary. Generally, the composition of this invention can produce remarkable therapeutic effects 1–3 days after beginning of use, with symptoms improved significantly even disappearing, and pH values in the vagina reduced to normal levels and the Gram-positive bacilli in the vagina restored to dominance in the vaginal bacterial flora, at which time therapy with the composition should be stopped or the dosage be reduced, or the treatment continued at a low maintenance dosage.

For the method of this invention, the patients are provided with the composition containing only the saccharides of this invention as active ingredients, or the composition containing the saccharides, anti-fungal agent and/or anti-bacterial agent. Alternatively, the composition containing the saccharides of this invention as its active ingredients is administered in conjunction with suitable anti-fungal agent or anti-bacterial agent. For the latter case, the composition of this invention can be administered simultaneously with the anti-fungal and/or anti-bacterial agent or before/after the administration of the anti-fungal and/or anti-bacterial agent.

After the administration of this composition, the clinical symptoms of patients can be alleviated quickly, the numbers of Gram-positive bacilli are increased in the vagina, vaginal acidity is raised with the pH value reduced to 4.0–4.6, while the Gram-negative bacilli, Gram-negative cocci and other harmful abnormal bacteria are reduced substantially or even disappear. The composition of this invention is easy to prepare and to use with reliable effects.

EXPERIMENTAL EXAMPLE 1

Experiment in vitro with the composition of this invention: The effect of the composition in promoting the growth of Gram-positive bacilli and the production of acids.

Method:

(1) The preparation of the composition: Sucrose was used to prepare the following composition according to the method mentioned above: sucrose 10.0% (W/V), yeast extract 1.0% (W/V), Xanthan gum 1.6% (W/V), pH 5.0; then filled the composition into the tubes after sterilization, with each tube containing 5 ml, and pre-reduced for use.

(2) Specimen suspension: Vaginal secretion was taken from one of the patients suffering from typical bacterial vaginosis with a cotton swab, then the swab was washed in 2 ml sterilized Trypcase-soy Broth immediately, and thus the specimen suspension was ready. The vaginal Gram smear showed few Gram-positive bacilli but an abundance of Gram-negative bacilli, negative cocci and positive cocci.

(3) The above-mentioned specimen suspension was inoculated immediately into the tubes containing the above-mentioned composition, 10 microliter for each tube, mixed homogeneously. The tubes were placed in an incubator for cultivation, at 37° C., anaerobically. Then, culture samples were taken from the tubes at 10 hours and 24 hours later respectively. The Gram smears of the samples were observed and the pH values of the samples were measured.

Results:

As shown in Table 1, although the Gram smear of the specimen showed few Gram-positive bacilli, the Gram positive bacilli grew remarkably in the composition of this invention after specimen suspension inoculated and cultivated. Meanwhile the pH value of the composition decreased.

TABLE 1

The Effect of the Composition of this Invention in Promoting the Growth of Gram-positive Bacilli and Producing Acids

| Sacchride contained in composition | Bacteria specimen suspension | in pH of the composition | 10 hours-culture | | 24 hours-culture | |
|---|---|---|---|---|---|---|
| | | | Bacteria | pH | Bacteria | pH |
| Sucrose | G + b*, −** G − b, ++++ | 5.0 | G + b, +++ G − b, ++ | 5.0 | G + b, ++++ G − b, ++ | 4.0 |

TABLE 1-continued

The Effect of the Composition of this Invention in Promoting the
Growth of Gram-positive Bacilli and Producing Acids

| Sacchride contained in composition | Bacteria specimen suspension | in pH of the composition | 10 hours-culture | | 24 hours-culture | |
|---|---|---|---|---|---|---|
| | | | Bacteria | pH | Bacteria | pH |
| | G − c, +++ | | G + c, + | | G − c, + | |
| | G + C, ++ | | G + C, ++ | | G + C, ++ | |

*G + b: Gram-positive bacilli,
G − b: Gram-negative bacilli;
G + c: Gram-positive cocci,
G − c: Gram-negative cocci.
**−: No or less than one bacterium per field of version under oil-immersion lens;
+: 1–9 bacteria per field of vision under oil-immersion lens;
++: About 10–99 bacteria per field of vision under oil-immersion lens;
+++: About 100 bacteria or more per field vision under oil-immersion lens, even uncountable;
++++: Bacteria clumped or aggregated.

Conclusion:

The composition of this invention has the effect of promoting the growth of Gram-positive bacilli and the production of the acids.

EXPERIMENT EXAMPLE 2

Experiment in vitro with the compositions of this invention: the comparison of the effects of compositions containing sucrose or maltose, and those containing other saccharides in promoting the growth of Gram-positive bacilli and the production of acids Method:

(1) The preparation of the compositions: Different saccharides were used respectively to prepare the following compositions according to the methods mentioned above: glucose, fructose, galactose, mannose, maltose, sucrose, lactose, lactulose, mycose, cellobiose, melibiose, melitose, malto-oligosaccharide, isomaltooligosaccharide and fructooligosaccharide, dextrin, starch, and glycogen:

A. 5% glucose, 1.0% yeast extract, 1.6% xanthan gum, pH adjusted to 6.2;
B. 5% fructose, 1.0% yeast extract, 1.6% xanthan gum, pH adjusted to 6.2;
C. 5% galactose, 1.0% yeast extract, 1.6% xanthan gum, pH adjusted to 6.2;
D. 5% mannose, 1.0% yeast extract, 1.6% xanthan gum, pH adjusted to 6.2;
E. 10.0% maltose, 1.0% yeast extract, 1.6% xanthan gum, pH adjusted to 6.2;
F. 10.0% sucrose, 1.0% yeast extract, 1.6% xanthan gum, pH adjusted to 6.2;
G. 10.0% lactose, 1.0% yeast extract, 1.6% xanthan gum, pH adjusted to 6.2;
H. 10.0% lactulose, 1.0% yeast extract, 1.6% xanthan gum, pH adjusted to 6.2;
I. 10.0% cellobiose, 1.0% yeast extract, 1.6% xanthan gum, pH adjusted to 6.2;
J. 10.0% mycose, 1.0% yeast extract, 1.6% xanthan gum, pH adjusted to 6.2;
K. 10.0% melibiose, 1.0% yeast extract, 1.6% xanthan gum, pH adjusted to 6.2;
L. 10.0% melitose, 1.0% yeast extract, 1.6% xanthan gum, pH adjusted to 6.2;
M. 10.0% maltooligosaccharide, 1.0% yeast extract, 1.6% xanthan gum, pH adjusted to 6.2;
N. 10.0% isomaltooligosaccharide, 1.0% yeast extract, 1.6% xanthan gum, pH adjusted to 6.2;
O. 10.0% fructooligosaccharide, 1.0% yeast extract, 1.6% xanthan gum, pH adjusted to 6.2;
P. 10.0% dextrin, 1.0% yeast extract, 0.5% xanthan gum, pH adjusted to 6.2;
Q. 10.0% starch, 1.0% yeast extract, pH adjusted to 6.2;
R. 10.0% glycogen, 1.0% yeast extract, 1.6% xanthan gum, pH adjusted to 6.2.

(2) The preparation of the test tubes: The compositions prepared above were filled into test tubes, with each tube containing 5 ml, sterilized, and kept until use for experiment.

(3) Specimen suspension: Vaginal secretion was taken from one of the patients suffering from typical bacterial vagmosis with a cotton swab, then the swab was washed in 2 ml sterilized Trypcase-soy Broth immediately, and thus the specimen suspension was ready. The vaginal Gram smear showed few Gram-positive bacilli but an abundance of Gram-negative bacilli, negative cocci and positive cocci.

(4) The specimen suspension was inoculated immediately into the tubes containing the above-mentioned compositions, 10 microliter for each tube, mixed homogeneously. Then the tubes were placed in a candle jar and cultivated at 37° C. After 24 hours and 48 hours' culture, culture samples were taken respectively from each of the tubes, then the Gram smears of the samples were observed and the pH values of culture samples were tested.

Results:

(1) As shown in Table 2, although there was few Gram positive bacilli in the vaginal secretion specimen, the Gram positive bacilli grew remarkably in the compositions containing different sugars of this invention after the compositions were inoculated with specimen suspension and cultivated for 24 hours or 48 hours. Meanwhile the pH values in most of the composition tubes decreased to different levels. These results indicate that sucrose, maltose, or any other kind of saccharides compatible to them according to this invention exerts respectively effect in promoting the growth of Gram-positive bacilli.

(2) As shown in Table 2, the fact that the pH values in 10% maltose tube and in 10% sucrose tube were lower than that of the other tubes after 24 or 48 hours culture indicates that maltose and sucrose are metabolized rapidly by bacteria. And maltose and sucrose exert better effect in promoting the growth of Gram-positive bacilli and the production of acids than that of the other kinds of oligosaccharides.

TABLE 2

Effects of Sucrose, Maltose and Other Saccharides on
Gram-positive Bacilli Growth and Acids-producing

| Sacchride contained in composition | Bacteria in specimen suspension | PH of the composition | 24 hours-culture Bacteria | pH | 48 hours-culture Bacteria | pH |
|---|---|---|---|---|---|---|
| Glucose | G + b, − | 6.2 | G + b, ++ | 6.4 | G + b, +++ | 6.2 |
|  | G − b, ++++ |  | G − b, + |  | G − b, + |  |
|  | G − c, +++ |  | G − c, − |  | G − c, − |  |
|  | G + c, ++ |  | G + c, − |  | C + c, ++ |  |
| Fructose | G + b, − | 6.2 | G + b, ++ | 5.4–5.8 | G + b, +++ | 5.4–5.8 |
|  | G − b, ++++ |  | G − b, + |  | G − b, + |  |
|  | G − c, +++ |  | G − c, − |  | G − c, − |  |
|  | G + c, ++ |  | G + c, + |  | G + c, + |  |
| Galactose | G + b, − | 6.2 | G + b, ++ | 6.7 | G + b, + | 6.7 |
|  | G − b, ++++ |  | G − b, − |  | G − b, + |  |
|  | G − c, +++ |  | G − c, − |  | G − c, − |  |
|  | G + c, ++ |  | G + c, ++ |  | G + c, ++ |  |
| Mannose | G + b, − | 6.2 | G + b, ++ | 6.4 | G + b, +++ | 5.8 |
|  | G − b, ++++ |  | G − b, + |  | G − b, + |  |
|  | G − c, +++ |  | G − c, − |  | G − c, − |  |
|  | G + c, ++ |  | G + c, ++ |  | G + c, + |  |
| Maltose | G + b, − | 6.2 | G + b, ++ | 4.6–48 | G + b, +++ | 4.4–4.6 |
|  | G − b, ++++ |  | G − b, +++ |  | G − b, ++ |  |
|  | G − c, +++ |  | G − c, − |  | G − c, − |  |
|  | G + c, ++ |  | G + c, ++ |  | G + c, + |  |
| Sucrose | G + b, − | 6.2 | G + b, ++ | 4.8–5.1 | G + b, +++ | 4.6–4.8 |
|  | G − b, ++++ |  | G − b, + |  | G − b, ++ |  |
|  | G − c, +++ |  | G − c, − |  | G − c, − |  |
|  | G + c, ++ |  | G + c, + |  | G + c, + |  |
| Lactose | G + b, − | 6.2 | G + b, ++ | 5.8 | G + b, ++ | 5.1–5.4 |
|  | G − b, ++++ |  | G − b, + |  | G − b, + |  |
|  | G − c, +++ |  | G − c, − |  | G − c, − |  |
|  | G + c, ++ |  | G + c, +++ |  | G + c, + |  |
| Lactulose | G + b, − | 6.2 | G + b, +++ | 5.8–6.2 | G + b, ++ | 6.2 |
|  | G − b, ++++ |  | G − b, + |  | G − b, + |  |
|  | G − c, +++ |  | G − c, − |  | G − c, − |  |
|  | G + c, ++ |  | G + c, + |  | G + c, + |  |
| Cellobiose | G + b, − | 6.2 | G + b, ++ | 5.8 | G + b, ++ | 5.8 |
|  | G − b, ++++ |  | G − b, + |  | G − b, + |  |
|  | G − c, +++ |  | G − c, − |  | G − c, − |  |
|  | G + c, ++ |  | G + c, + |  | G + c, + |  |
| Mycose | G + b, − | 6.2 | G + b, ++ | 4.8 | G + b, +++ | 4.6–4.8 |
|  | G − b, ++++ |  | G − b, + |  | G − b, ++ |  |
|  | G − c, +++ |  | G − c, − |  | G − c, − |  |
|  | G + c, ++ |  | G + c, + |  | G + c, + |  |
| Melibiose | G + b, − | 6.2 | G + b, + | 6.2 | G + b, ++ | 5.8 |
|  | G − b, ++++ |  | G − b, ++ |  | G − b, ++ |  |
|  | G − c, +++ |  | G − c, + |  | G − c, − |  |
|  | G + c, ++ |  | G + c, + |  | G + c, + |  |
| Melitose | G + b, − | 6.2 | G + b, ++ | 6.7 | G + b, +++ | 5.8 |
|  | G − b, ++++ |  | G − b, + |  | G − b, ++ |  |
|  | G − c, +++ |  | G − c, + |  | G − c, − |  |
|  | G + c, ++ |  | G + c, + |  | G + c, + |  |
| Maltooligo-Sacchride | G + b, − | 6.2 | G + b, ++ | 5.8 | G + b, +++ | 5.8 |
|  | G − b, ++++ |  | G − b, + |  | G − b, + |  |
|  | G − c, +++ |  | G − c, − |  | G − c, − |  |
|  | G + c, ++ |  | G + c, ++ |  | G + c, ++ |  |
| Fructooligo-saccharide | G + b, − | 6.2 | G + b, +++ | 5.8 | G + b, +++ | 6.2 |
|  | G − b, ++++ |  | G − b, ++ |  | G − b, + |  |
|  | G − c, +++ |  | G − c, − |  | G − c, − |  |
|  | G + c, ++ |  | G + c, + |  | G + c, − |  |
| Isomaltooligo-Saccharide | G + b, − | 6.2 | G + b, ++ | 6.2 | G + b, +++ | 5.8 |
|  | G − b, ++++ |  | G − b, ++ |  | G − b, ++ |  |
|  | G − c, +++ |  | G − c, − |  | G − c, − |  |
|  | G + c, ++ |  | G + c, + |  | G + c, + |  |
| Dextrin | G + b, − | 6.2 | G + b, +++ | 6.2 | G + b, ++ | 5.8 |
|  | G − b, ++++ |  | G − b, ++ |  | G − b, + |  |
|  | G − c, +++ |  | G − c, − |  | G − c, − |  |
|  | G + c, ++ |  | G + c, + |  | G + c, − |  |
| Starch | G + b, − | 6.2 | G + b, ++ | 6.7 | G + b, ++ | 6.2 |
|  | G − b, ++++ |  | G − b, ++ |  | G − b, ++ |  |
|  | G − c, +++ |  | G − c, − |  | G − c, − |  |
|  | G + c, ++ |  | G + c, + |  | G + c, + |  |

TABLE 2-continued

Effects of Sucrose, Maltose and Other Saccharides on Gram-positive Bacilli Growth and Acids-producing

| Sacchride contained in composition | Bacteria in specimen suspension | PH of the composition | 24 hours-culture Bacteria | pH | 48 hours-culture Bacteria | pH |
|---|---|---|---|---|---|---|
| Glycogen | G + b, −<br>G − b, ++++<br>G − c, +++<br>G + c, ++ | 6.2 | G + b, ++<br>G − b, ++<br>G − c, −<br>G + c, + | 6.4 | G + b, +++<br>G − b, ++<br>G − c, −<br>G + c, + | 6.2 |

Conclusion:

The sugar components contained in the compositions of this invention can be sucrose, maltose or the both or mixtures of sucrose and/or maltose and other saccharides as defined above.

EXPERIMENT EXAMPLE 3

Experiment in vitro with the compositions of this invention: The effects of the compositions of this invention in promoting the growth of Gram-positive bacilli and the production of acids.

Methods:
(1) The preparation of the compositions: Maltose and sucrose were used respectively to prepare the following composition according to the methods mentioned above:
 A. 2.5% maltose, 1.0% yeast extract, 1.6% xanthan gum, pH adjusted to 6.2;
 B. 2.5% sucrose, 1.0 yeast extract, 1.6% xanthan gum, pH adjusted to 6.2;

(2) The preparation of the test tubes: Compositions as prepared above were filled into the test tubes, with each tube containing 5 ml, sterilized, and kept until use for experiment.
(3) Specimen suspension: Vaginal secretion was taken from one of the patients suffering from typical bacterial vaginosis with a cotton swab, then the swab was washed in 2 ml sterilized Trypcase-soy Broth immediately, and thus the specimen suspension was ready. The vaginal Gram smear showed few Gram-positive bacilli but an abundance of Gram-negative bacilli, negative cocci and positive cocci.
(4) The above-mentioned specimen suspension was inoculated immediately into the tubes containing the above-mentioned compositions, 10 microliter for each tube, mixed homogeneously. Then the tubes were placed in a candle jar and cultivated at 37° C. After 24 hours and 48 hours' culture, culture samples were taken respectively from each of the tubes, then the Gram smears of the samples were observed and the pH values of culture samples were tested.

Results:

As shown in Table 3, although there was few Gram positive bacilli in the vaginal secretion specimen, the Gram positive bacilli grew in the compositions containing different sugars of this invention after the compositions were inoculated with specimen suspension and cultivated for 24 hours or 48 hours. It indicates that 2.5% of sucrose and 2.5% of maltose have the effects in promoting the growth of Gram-positive bacilli.

TABLE 3

The Effect of the Compositions of This Invention in Promoting the Growth of Gram-positive Bacilli and the Production of Acids

| Saccharde contained in composition | Bacteria in specimen suspension | PH of the composition | 24 hours-culture Bacteria | pH | 48 hours-culture Bacteria | pH |
|---|---|---|---|---|---|---|
| Maltose | G + b, −<br>G − b, ++++<br>G − c, +++<br>G + c, ++ | 6.2 | G + b, +<br>G − b, +++<br>G − c, −<br>G + c, − | 7.0 | G + b, +++<br>G − b, +<br>G − c, −<br>G + c, + | 6.4 |
| Sucrose | G + b, −<br>G − b, ++++<br>G − c, +++<br>G + c, ++ | 6.2 | G + b, +<br>G − b, +<br>G − c, −<br>G + c, + | 6.2 | G + b, +<br>G − b, ++<br>G − c, −<br>G + c, + | 6.7 |

Conclusion:

The compositions of this invention containing 2.5% sucrose or maltose exert certain effects in promoting the growth of Gram-positive bacilli.

EXPERIMENT EXAMPLE 4

Experiment in vitro with the compositions of this invention: effects of the compositions of this invention in promoting the growth of Gram-positive bacilli and the production of acids.

Method:
(1)The preparation of the compositions: Maltose and sucrose were used respectively to prepare the following composition in the methods mentioned above:

A. 17.0% maltose, 1.0% yeast extract, 1.6% xanthan gum, pH adjusted to 6.2;
B. 17.0% sucrose, 1.0% yeast extract, 1.6% xanthan gum, pH adjusted to 6.2;
(2) The preparation of the test tubes: Compositions prepared above were filled into the test tubes, with each tube containing 5 ml, sterilized, and kept until use for experiment.
(3) Specimen suspension: Vaginal secretion was taken from one of the patients suffering from typical bacterial vaginosis with a cotton swab, then the swab was washed in 2 ml sterilized Trypcase-soy Broth immediately, and thus the specimen suspension was ready. The vaginal Gram smear showed few Gram-positive bacilli but an abundance of Gram-negative bacilli, negative cocci and positive cocci.
(4) The above-mentioned specimen suspension was inoculated immediately into the tubes containing the above-prepared compositions, 10 microliter for each tube, mixed homogeneously. Then the tubes were placed in a candle jar and cultivated at 37° C. After 24 hours and 48 hours' culture, culture samples were taken respectively from each of the tubes, then the Gram smears of the samples were observed and the pH values of culture samples were tested.

Results:

As shown in Table 4, although there was few Gram positive bacilli in the vaginal secretion specimen, numerous Gram positive bacilli grew in the compositions of this invention after the compositions were inoculated with specimen suspension and cultivated for 24 hours or 48 hours. Meanwhile the pH values of the composition tubes decreased remarkably. These results indicate that compositions containing 17% of sugars of this invention exert remarkable effect in promoting the growth of Gram-positive bacilli.

A. 10.0% maltose, 1.0% yeast extract, 1.6% xanthan gum, pH adjusted to 4.4;
B. 10.0% maltose, 1.0% yeast extract, 1.6% xanthan gum, pH adjusted to 4.8;
C. 10.0% maltose, 1.0% yeast extract, 1.6% xanthan gum, pH adjusted to 5.1;
D. 10.0% maltose, 1.0% yeast extract, 1.6% xanthan gum, pH adjusted to 5.4;
E. 10.0% maltose, 1.0% yeast extract, 1.6% xanthan gum, pH adjusted to 5.8;
F. 10.0% maltose, 1.0% yeast extract, 1.6% xanthan gum, pH adjusted to 6.4;
G. 10.0% maltose, 1.0% yeast extract, 1.6% xanthan gum, pH adjusted to 6.8;
H. 10.0% maltose, 1.0% yeast extract, 1.6% xanthan gum, pH adjusted to 7.2;
(2) The preparation of the test tubes: Compositions prepared above were filled into the test tubes, with each tube containing 5 ml, sterilized, and kept until use for experiments.
(3) Specimen suspension: Vaginal secretion was taken from one of the patients suffering from typical bacterial vaginosis with a cotton swab, then the swab was washed in 2 ml sterilized Trypcase-soy Broth immediately, and thus the specimen suspension was ready. The vaginal Gram smear showed few Gram-positive bacilli but an abundance of Gram-negative bacilli, negative cocci and positive cocci.
(4) The above-mentioned specimen suspension was inoculated immediately into the tubes containing the above-mentioned compositions, 10 microliter for each tube, mixed homogeneously. Then the tubes were placed in a candle jar and cultivated at 37° C. After 24 hours and 48 hours' culture, culture samples were taken respectively from each of the tubes, then the Gram smears of the

TABLE 4

Selective Promoting Effect on the Growth of Gram-positive Bacilli and the Production of acids

| Saccharide contained in the preparation | Bacteria in specimen inoculated | pH of the preparation | 24 hours culture Bacteria | pH | 48 hours culture Bacteria | pH |
|---|---|---|---|---|---|---|
| Maltose | G + b, −    | 6.2 | G + b, +++ | 5.4 | G + b, ++ | 5.1 |
|         | G − b, ++++ |     | G − b, +   |     | G − b, ++ |     |
|         | G − c, +++  |     | G − c, −   |     | G − c, −  |     |
|         | G + c, ++   |     | G + c, +   |     | G + c, ++ |     |
| Sucrose | G + b, −    | 6.2 | G + b, ++  | 6.2 | G + b, ++ | 5.4 |
|         | G − b, ++++ |     | G − b, ++  |     | G − b, ++ |     |
|         | G − c, +++  |     | G − c, −   |     | G − c, −  |     |
|         | G + c, ++   |     | G + c, +   |     | G + c, ++ |     |

Conclusion:

The compositions of this invention containing 17% sucrose or maltose exert effects in promoting the growth of Gram-positive bacilli.

EXPERIMENT EXAMPLE 5

Experiment in vitro with the compositions of this invention: The influence of different pH values on the effects of the compositions of this invention on the growth of Gram-positive bacilli and the production of acids.
Method:
(1) The preparation of the compositions: Maltose was used to prepare the following compositions according to the method mentioned above:

samples were observed and the pH values of culture samples were tested.
Results:
As shown in Table 5,
(1) When the pH value of the composition of this invention was 4.4, a few of Gram-positive bacilli grew in the composition after 48 hours' culture.
(2) When the pH values of the compositions of this invention were 5.4–7.2, the Gram-positive bacilli grew very well. Gram-positive bacilli grew and the pH values decreased after 24 hours' culture and the bacilli were numerous and the pH values decreases to about 4.1–4.4 after 48 hours' culture.

TABLE 5

The Influence of Different pH values of the Compositions of This Invention on the Treatment Effects

| Saccharide contained in the composition | Bacteria in specimen inoculated | pH of the composition | 24 hours culture Bacteria | pH | 48 hours culture Bacteria | pH |
|---|---|---|---|---|---|---|
| Maltose | G + b, −<br>G − b, ++++<br>G − c, +++<br>G + c, ++ | 4.4 | G + b, −~+<br>G − b, ++<br>G − c, −<br>G + c, − | 4.4 | G + b, −~+<br>G − b, ++<br>G − c, −<br>G + c, − | 4.4 |
| Maltose | G + b, −<br>G − b, ++++<br>G − c, +++<br>G + c, ++ | 4.8 | G + b, +<br>G − b, ++<br>G − c, −<br>G + c, + | 4.8 | G + b, +<br>G − b, ++<br>G − c, −<br>G + c, + | 4.4–4.8 |
| Maltose | G + b, −<br>G − b, ++++<br>G − c, +++<br>G + c, ++ | 5.1 | G + b, +<br>G − b, ++<br>G − c, −<br>G + c, + | 4.6 | G + b, ++<br>G − b, ++<br>G − c, −<br>G + c, ++ | 4.4–4.6 |
| Maltose | G + b, −<br>G − b, ++++<br>G − c, +++<br>G + c, ++ | 5.4 | G + b, +++<br>G − b, +<br>G − c, −<br>G + c, + | 5.4 | G + b, ++<br>G − b, ++<br>G − c, −<br>G + c, − | 4.1–4.4 |
| Maltose | G + b, −<br>G − b, ++++<br>G − c, +++<br>G + c, ++ | 5.8 | G + b, ++<br>G − b, ++<br>G − c, −<br>G + c, + | 4.8 | G + b, +++<br>G − b, ++<br>G − c, −<br>G + c, + | 4.1 |
| Maltose | G + b, −<br>G − b, ++++<br>G − c, +++<br>G + c, ++ | 6.4 | G + b, +<br>G − b, ++<br>G − c, −<br>G + c, + | 4.4 | G + b, +++<br>G − b, ++<br>G − c, −<br>G + c, + | 4.1 |
| Maltose | G + b, −<br>G − b, ++++<br>G − c, +++<br>G + c, ++ | 6.8 | G + b, ++<br>G − b, ++<br>G − c, −<br>G + c, − | 5.4 | G + b, +++<br>G − b, ++<br>G − c, −<br>G + c, + | 4.4 |
| Maltose | G + b, −<br>G − b, ++++<br>G − c, +++<br>G + c, ++ | 7.2 | G + b, ++<br>G − b, +<br>G − c, −<br>G + c, − | 5.4 | G + b, +++<br>G − b, ++<br>G − c, −<br>G + c, − | 4.1 |

Conclusion:

In this in vitro experiment, the compositions of this invention with pH values of 5.4–7.2 exerted stronger effects in promoting the growth of Gram-positive bacilli.

EXPERIMENT EXAMPLE 6

Case Report

Ms. Jiang, female, aged 30. Her vaginal secretions had exhibited unpleasant fish-odor accompanying pruritus of vulvae for 2 years. Examined and diagnosed as "bacterial vaginosis" by the present inventor. The patient was treated with a composition containing 12% (W/V) of lactose and having pH value of 5.0. The drug was intravaginally administered, 3 ml for each time, once a day. After the treatment continued successively for three days, the pH value of the vaginal secretions of this patient decreased from 5.4 to 4.6. But the Gram smears showed that the majority of the bacteria were still Gram-negative bacilli, and there were also a lot of positive cocci and positive bacilli. Thus, the drug for treatment was changed to a composition of this invention containing 12% (W/V) of maltose, with the pH value 5.0. 10 hours after the administration of 3 ml of the latter composition, the pH value of the vaginal secretions of the patient decreased to 3.8. Then the dose was reduced to 2 ml of the composition for each time, once a day. The pH values of the vaginal swabs were maintained at normal levels (pH<4.6). Afterwards, the illness of this patient relapsed after the menstruation several times, and the abnormal bacterial flora and the decreased vaginal acidity of this patient after the menstruation restored to normal states by the intravaginal administration of the composition of this invention containing 12% (W/V) of maltose.

EXPERIMENT EXAMPLE 7

Experiment in vivo with the composition of the present invention: the influences of the composition of this invention on the vaginal bacterial flora of rhesus macaques.

Experimental Method:

(1) Animals: Took the vaginal swabs of ten female macaques, tested the pH values and carried out Gram smears examination. The results showed that in eight rhesus macaques, the pH values of the vaginal swabs were greater than 4.6 and Gram smears revealed few Gram-positive bacilli, a lot of Gram-negative bacilli and negative cocci, alike the bacterial flora of bacterial vaginosis in human beings. In the two left rhesus macaques, the pH values of the vaginal swabs were lower than 4.6 and the bacteria revealed on Gram smears were Gram-positive bacilli, alike the bacterial flora of the normal vaginal bacterial flora of human beings.

(2) In the 8 rhesus macaques, the vaginal bacterial flora were the type of bacterial vaginosis of human beings. 3 of them were excluded from the experiment because of menstruation. The other 5 rhesus macaques were included in the experiment.

(3) Composition: A composition of this invention was used, which contained 12% (W/V) of sucrose, 1% (W/V) of yeast extract, 1.6% (W/V) of xanthan gum and its' pH value was 5.1.

(4) Administration: 1 ml of the above-mentioned composition of this invention was administrated intravaginally, twice a day. When most of the vaginal bacteria was changed to Gram-positive bacilli, the dose was reduced or the treatment stopped. In this experiment, 1 macaque received the composition only once, 2 macaques twice, and the other 2 macaques three times.

(5) Result examination: Took the vaginal swabs before each dosage was administered to detect the pH values and to perform Gram smears examination. Thus the change of the vaginal bacterial flora of the macaques was monitored.

Result:

After the treatment with the composition of the present invention, the vaginal pH values were reduced to 3.8–4.1 and the vaginal bacterial floras were changed to be dominated with Gram-positive bacilli in all the five macaques. This result indicates that the composition of this invention has very strong effects in vivo in promoting the growth of Gram-positive bacilli and the production of acids.

ADVANTAGES OF THIS INVENTION COMPARED TO THE PRIOR ART

Advantages Compared to Anti-bacterial Treatments:

Anti-bacterial drugs, based on the views of etiology, control the abnormal bacteria that grow excessively and cause pathological reaction by killing or suppressing such bacteria. This method has the following shortcomings: (1) After repeated treatments with anti-bacterial drugs, the bacteria may gain drug-resistances which may lead to the failure of antibacterial therapy. (2) Anti-bacterial treatment may result in the superinfection by drug-resistant bacteria. (3) Anti-bacterial drugs may be allergic to human body and may have other kinds of adverse effects to skin or vaginal mucous membrane. Compositions containing lactic acid or acetic acid or other selective bacterial inhibitors as its active ingredients, for example, the compositions described in the patent applications Nos. GB21 12285A and EP-A-0257007, exert strong prohibition effects on the pathogens and have no remarkable prohibition effects on lactobacilli. Thus they may exert indirectly the favorable effects on the growth of lactobacilli in the vagina. The compositions themselves, however, cannot directly and remarkably promote the growth of lactobacilli in the vagina. The effects of these compositions in increasing the acidity in the vagina last only for a short period of time, and it is very hard for the physiological Gram-positive bacilli to restore and dominate over the vaginal bacterial flora.

The compositions of this invention can stimulate the growth of Gram-positive bacilli and increase acidity in the vagina, and thus suppress Gram-negative bacilli, Gram negative cocci, and Gram-positive cocci thereby. Seen from above analysis, the technologies and compositions of this invention actually enhance the natural physiological anti-disease mechanisms in the vagina and fundamentally avoid and overcome the disadvantages of the disturbance of vaginal bacterial flora by anti-bacterial treatment, therefore have remarkable advantages.

Advantages Compared to Lactobacilli Preparations:

Firstly, the effects of lactobacilli preparations in the treatment of severe disturbance of the vaginal bacterial flora, such as typical bacterial vaginosis. are often variable. Secondly, the lactobacilli preparations are more difficult to produce and store in addition to its high production cost. The compositions of this invention have a lower cost of production and longer effective period, and are significantly superior over the lactobacilli preparations. Moreover, the compositions of this invention improve the condition of the local micro-habitat in the vagina thus promote the growth of the endogenous Gram—positive bacilli in the vagina. It should be better than the direct supplement of the exogenous lactobacilli strains.

COMPOSITION EXAMPLES

EXAMPLE 1

2.5 g of sucrose and 2.0 g xanthan gum were mixed homogeneously. Then to the resultant mixture, some distilled water is added while stirring in order to dissolve the sugar component and swell the xanthan gum to homogeneous viscous gum. By adding a suitable amount of lactic acid, the pH of the solution was adjusted to 5.0. Distilled water was added until the total volume of the solution is equal to 100 ml. The resulting solution is sterilized by means of intermittent sterilization.

EXAMPLE 2

100 ml of the composition in the following formulation was prepared substantially according to the method as described in Example 1, except that the pH value is adjusted with 0.5 N sodium hydroxide.

| | |
|---|---|
| Sucrose | 17.0% (W/V) |
| Yeast extract powder | 1.0% (W/V) |
| Xanthan gum | 1.5% (W/V) |
| Distilled water | q.s. |
| pH | 7.2 |

EXAMPLE 3

100 ml of the composition in the following formulation was prepared substantially according to the method as described in Example 1.

| | |
|---|---|
| Sucrose | 12.0% (W/V) |
| Yeast extract powder | 1.0% (W/V) |
| Xanthan gum | 1.0% (W/V) |
| Distilled water | q.s. |
| pH | 4.1 |

EXAMPLE 4

100 ml of the composition in the following formulation was prepared substantially according to the method as described in Example 1.

| | |
|---|---|
| Sucrose | 4.0% (W/V) |
| Maltose | 5.0% (W/V) |
| Fructose | 2.0 (W/V) |
| Histidine | 100 ppm |
| Methionine | 50.0 ppm |
| Riboflavin | 0.2 ppm |
| Thiamine | 0.2 ppm |
| Nicotinic acid | 0.2 ppm |
| Calcium pantothenate | 0.2 ppm |
| Xanthan gum | 1.5% (W/V) |
| Distilled water | q.s. |
| pH | 6.4 |

EXAMPLE 5

100 ml of the composition in the following formulation was prepared substantially according to the method as described in Example 1.

| | |
|---|---|
| Maltose | 2.5% (W/V) |
| Xanthan gum | 1.6% (W/V) |
| Distilled water | q.s. |
| pH | 6.8 |

EXAMPLE 6

100 ml of the composition in the following formulation was prepared substantially according to the method as described in Example 1.

| | |
|---|---|
| Maltose | 17.0% (W/V) |
| Xanthan gum | 1.6% (W/V) |
| Yeast extract | 1.0% (W/V) |
| Distilled water | q.s. |
| pH | 5.4 |

EXAMPLE 7

100 ml of the composition in the following formulation was prepared substantially according to the method as described in Example 1.

| | |
|---|---|
| Maltose | 13.0% (W/V) |
| Yeast extract | 1.0% (W/V) |
| Xanthan gum | 1.6% (W/V) |
| Distilled water | q.s. |
| pH | 6.4 |

EXAMPLE 8

100 ml of the composition in the following formulation was prepared substantially according to the method as described in Example 1.

| | |
|---|---|
| Maltose | 10.0% (W/V) |
| Glucose | 2.0% (W/V) |
| Yeast extract | 1.0% (W/V) |
| Xanthan gum | 1.6% (W/V) |
| Distilled water | q.s. |
| pH | 4.8 |

EXAMPLE 9

100 ml of the composition in the following formulation was prepared substantially according to the method as described in Example 1.

| | |
|---|---|
| Sucrose | 12.0% (W/V) |
| Glucose | 1.0% (W/V) |
| Yeast extract | 0.S% (W/V) |
| Xanthan gum | 1.7% (W/V) |
| Distilled water | q.s. |
| pH | 5.6 |

EXAMPLE 10

100 ml of the composition in the following formulation was prepared substantially according to the method as described in Example 1.

| | |
|---|---|
| Sucrose | 10.0% (W/V) |
| Glucose | 1.0% (W/V) |
| Histidine | 100 ppm |
| Methionine | 50.0 ppm |
| Riboflavin | 0.2 ppm |
| Thiamine | 0.2 ppm |
| Nicotinic acid | 0.2 ppm |
| Calcium pantothenate | 0.2 ppm |
| Xanthan gum | 1.8% (W/V) |
| Distilled water | q.s. |
| pH | 6.5 |

EXAMPLE 11

100 ml of the composition in the following formulation was prepared substantially according to the method as described in Example 1.

| | |
|---|---|
| Maltose | 10.0% (W/V) |
| Ketoconazole | 2.0% (W/V) |
| Yeast extract | 1.0% (W/V) |
| Xanthan gum | 1.5% (W/V) |
| Distilled water | q.s. |
| PH | 6.0 |

EXAMPLE 12

100 ml of the composition in the following formulation was prepared substantially according to the method as described in Example 1.

| | |
|---|---|
| Maltose | 9.0% (W/V) |
| Polymyxin E | 0.5% (W/V) |
| Yeast extract | 1.0% (W/V) |
| Xanthan gum | 2.2% (W/V) |
| Distilled water | q.s. |
| pH | 6.3 |

FORMULATION EXAMPLE 1

100 ml of the composition in the following formulation is prepared basically in the methods as described in Example 1.

| | |
|---|---|
| Sucrose | 9.0% (W/V) |
| Fluconazole | 0.01% (W/V) |
| Xanthan gum | 1.5% (W/V) |

-continued

| | |
|---|---|
| Distilled water | 100 ml |
| PH | 7.0 |

FORMULATION EXAMPLE 2

100 ml of the composition in the following formulation is prepared basically in the methods as described in Example 1.

| | |
|---|---|
| Sucrose | 9.0% (W/V) |
| Terconazole | 0.04% (W/V) |
| Xanthan gum | 2.2% (W/V) |
| Distilled water | 100 ml |
| PH | 7.0 |

The compositions of this invention are simple in components and can be easily manufactured at low cost.

EXPERIMENTAL EXAMPLE 1

Materials and Methods
1. Materials:
   Sucrose Broth: 10.0% sucrose, 2.0% yeast extract, $K_2HPO_4$ 0.5%, $MgSO_4$ 0.05%, $MnSO_4$ 0.1%, pH adjusted to 6.2, sterilized.
   Anti-fungi drug: Fluconazole
   Clinically isolated Lactobacillus strains: *Lactobacillus acidophilus, Lactobacillus crispatus*, and *Lactobacillus jensenii*. Three lactobacillus suspensions were prepared separately from each of these three lactobacillus strains.
   Clinically isolated Candida strains: *Candida albicans* and *Candida tropicalis*. Two Candidal suspensions were prepared separately from each of these two candida strains.
2. Methods:
   Grouping: 24 tubes were divided into 3 lactobacillus strain groups and 1 Candidal group, as indicated in Table 1.

There were six tubes in each group and each tube contained 2ml Sucrose Broth and different concentration of Fluconazole, as shown in Table 1.

The turbidity values of three lactobacillus suspensions and two Candidal suspensions were tested by Turbidimeter and adjusted to 0.3. 50 ul of each prepared lactobacillus suspension and Candidal suspension were separately added into tubes according to Table 1.

All of these experimental tubes were put into candle jars as soon as the lactobacillus suspensions and candidal suspensions were added, and then incubated at 37° C. for 18 hours.

After 18 hours' incubation the turbidity of each tube was examined and Gram-stained smear of cultural fluid of corresponding tube was observed under microscopy to check microbes.

Results

The results are shown in Table 2.

1. The cultural fluids were turbid in three Lactobacillus groups that indicated microbial growth. Lactobacilli were observed on the Gram-stained smear of the cultural fluid of these three experimental groups. Lactobacilli and Candida were observed on the Gram-stained smear of the cultural fluid of control tubes. These results showed that 400 ug/ml of Fluconazole didn't inhibit the growth of three Lactobacillus strains but 25ug/ml or greater concentration of Fluconazole inhibited the growth of two Candidal strains.

TABLE 2

The Microbial Growth in Each Experimental Tubes

| Microbial growth in each tube | Tube1 | Tube2 | Tube3 | Tube4 | Tube5 | Control-tube |
|---|---|---|---|---|---|---|
| Group 1 | 400 | 200 | 100 | 50 | 25 | 0 |
| Turbidity | ++ | ++ | ++ | ++ | ++ | ++ |
| Microbes | Lb | Lb | Lb | Lb | Lb | Lb & C |

TABLE 1

Four Groups of Different Microbial Strains and Fluconazole Concentrations

| | Concentration of Fluconazole (ug/ml) | | | | | |
|---|---|---|---|---|---|---|
| Microbes of each group | Tube1 | Tube2 | Tube3 | Tube4 | Tube5 | Control-tube |
| Group 1<br>*L. acidophilus*<br>*C. albicans*<br>*C. tropicalis* | 400 | 200 | 100 | 50 | 25 | 0 |
| Group 2<br>*L. crispatus*<br>*C. albicans*<br>*C. tropicalis* | 400 | 200 | 100 | 50 | 25 | 0 |
| Group 3<br>*L. jensenii*<br>*C. albicans*<br>*C. tropicalis* | 400 | 200 | 100 | 50 | 25 | 0 |
| Group 4<br>*C. albicans*<br>*C. tropicalis* | 400 | 200 | 100 | 50 | 25 | 0 |

TABLE 2-continued

The Microbial Growth in Each Experimental Tubes

| Microbial growth in each tube | Tube1 | Tube2 | Tube3 | Tube4 | Tube5 | Control-tube |
|---|---|---|---|---|---|---|
| Group 2 | 400 | 200 | 100 | 50 | 25 | 0 |
| Turbidity | ++ | ++ | ++ | ++ | ++ | ++ |
| Microbes | Lb | Lb | Lb | Lb | Lb | Lb & C |
| Group 3 | 400 | 200 | 100 | 50 | 25 | 0 |
| Turbidity | ++ | ++ | ++ | ++ | ++ | ++ |
| Microbes | Lb | Lb | Lb | Lb | Lb | Lb & C |
| Group 4 | 400 | 200 | 100 | 50 | 25 | 0 |
| Turbidity | +/− | +/− | +/− | +/− | +/− | ++ |
| Microbes | − | − | − | − | − | C |

"++": The cultural fluid was heavily turbid;
"+": The cultural fluid was turbid;
"+/−": The turbidity of the cultural fluid was not affirmative;
"Lb": Lactobacilli;
"C": Candida.

2. In Group 4, the cultural fluids in experimental tubes was almost clear and no Candida was found. It was turbid in control tube and Microscopy examination of the cultural fluid revealed yeast-like organisms. That showed there was much less Candidal growth in experimental tubes than in control tube. It indicated that 25 ug/ml or greater concentration of Fluconazole inhibited the growth of the two Candidal strains.

Discussion

The results of this experiment proved that certain anti-fungi drug such as Fluconazole could prevent the growth of Candida but didn't inhibit the growth of Lactobacilli. Thus it is worthwhile to combine the Lactobacilli growth-promoting saccharides of this invention with anti-fungi drugs so as to promote the growth of vaginal lactobacilli while preventing the potential growth of Candida in the vagina.

Experimental Example 2

Materials and Methods

1. Materials:
    Maltose Broth: 10.0% maltose, 2.0% yeast extract, $K_2HPO_4$ 0.5%, $MgSO_4$ 0.05%, $MnSO_4$ 0.1%, pH adjusted to 6.2, sterilized.
    Anti-fungi drug: Terconazole
    Clinically isolated Lactobacillus strains: *Lactobacillus acidophilus, Lactobacillus crispatus*, and *Lactobacillus jensenii*. Three lactobacillus suspensions were prepared separately from each of these three lactobacillus strains.
    Clinically isolated Candida strains: *Candida albicans* and *Candida tropicalis*. Two Candidal suspensions were prepared separately from each of these two candida strains.
2. Methods:
    Grouping: 24 tubes were divided into 3 lactobacillus strain groups and 1 Candidal group, as indicated in Table 1.

TABLE 1

Four Groups of Different Microbial Strains and Terconazole Concentrations

| | Concentration of Terconazole (ug/ml) | | | | | |
|---|---|---|---|---|---|---|
| Microbes in each group | Tube1 | Tube2 | Tube3 | Tube4 | Tube5 | Control-tube |
| Group 1<br>*L. acidophilus*<br>*C. albicans*<br>*C. tropicalis* | 400 | 200 | 100 | 50 | 25 | 0 |
| Group 2<br>*L. crispatus*<br>*C. albicans*<br>*C. tropicalis* | 400 | 200 | 100 | 50 | 25 | 0 |
| Group 3<br>*L. jensenii*<br>*C. albicans*<br>*C. tropicalis* | 400 | 200 | 100 | 50 | 25 | 0 |
| Group 4<br>*C. albicans*<br>*C. tropicalis* | 400 | 200 | 100 | 50 | 25 | 0 |

There were six tubes in each group and each tube contained 2 ml Maltose Broth and different concentration of Terconazole, as shown in Table 1.
The turbidity values of three lactobacillus suspensions and two Candidal suspensions were tested by Turbidimeter and adjusted to 0.3. 50 ul of each prepared lactobacillus suspension and Candidal suspension were separately added into tubes according to Table 1.
All of these experimental tubes were put into candle jars as soon as the lactobacillus suspensions and candidal suspensions were added, and then incubated at 37° C. for 18 hours.
After 18 hours' incubation the turbidity of each tube was examined and Gram-stained smear of cultural fluid of corresponding tube was observed under microscopy to check microbes.

Results
The results are shown in Table 2.
1. The cultural fluids were turbid in three Lactobacillus groups that indicated microbial growth. Lactobacilli were observed on the Gram-stained smear of the cultural fluid of these three experimental groups. Lactobacilli and Candida were observed on the Gram-stained smear of the cultural fluid of control tubes. These results showed that 400 ug/ml of Terconazole didn't inhibit the growth of three Lactobacillus strains but 25 ug/ml or greater concentration of Terconazole inhibited the growth of two Candidal strains.

TABLE 2

The Microbial Growth in Each Experimental Tubes

| Microbial growth in each tube | Tube1 | Tube2 | Tube3 | Tube4 | Tube5 | Control-tube |
|---|---|---|---|---|---|---|
| Group 1 | 400 | 200 | 100 | 50 | 25 | 0 |
| Turbidity | ++ | ++ | ++ | ++ | ++ | ++ |
| Microbes | Lb | Lb | Lb | Lb | Lb | Lb & C |
| Group 2 | 400 | 200 | 100 | 50 | 25 | 0 |
| Turbidity | ++ | ++ | ++ | ++ | ++ | ++ |
| Microbes | Lb | Lb | Lb | Lb | Lb | Lb & C |
| Group 3 | 400 | 200 | 100 | 50 | 25 | 0 |
| Turbidity | ++ | ++ | ++ | ++ | ++ | ++ |
| Microbes | Lb | Lb | Lb | Lb | Lb | Lb & C |
| Group 4 | 400 | 200 | 100 | 50 | 25 | 0 |
| Turbidity | +/- | +/- | +/- | +/- | +/- | ++ |
| Microbes | - | - | - | - | - | C |

"++": The cultural fluid was heavily turbid;
"+": The cultural fluid was turbid;
"+/-": The turbidity of the cultural fluid was not affirmative;
"Lb": Lactobacilli;
"C": Candida In Group 4, the cultural fluids of experimental tubes seemed slightly turbid but no organism was found. It was turbid in control tube and Microscopy examination of the cultural fluid revealed yeast-like organisms. That showed there was much less Candidal growth in experimental tubes than in control tube. It showed that 25 ug/ml or greater concentration of Terconazole inhibited the growth of the two Candidal strains.

Discussion

The results of this experiment strongly proved that anti-fungi drugs such as Terconazole could prevent the growth of Candidal strains but didn't inhibit the growth of Lactobacilli. Thus it is worthwhile to combine the Lactobacilli growth-promoting saccharides of this invention with anti-fungi drugs so as to promote the growth of vaginal lactobacilli while preventing the potential growth of Candida in the vagina.

Case Example 3

Ms. Wang, female, aged 38. She had suffered pruritus of vulvae and unpleasant vaginal fish-odor for about 1 year. The inventor checked the patient's vaginal smear and found that there was mass of Gram-negative bacteria on Gram smears of her vaginal secretions. There were also a few Gram-positive cocci and yeast-like organisms. The vaginal pH value of this patient was 5.4. Diagnosed as "bacterial vaginosis" by the inventor, the patient was treated firstly with composition containing 10% (W/V) of sucrose. The drug was intra-vaginally administered, 2ml for each time, once a day. After the treatment continued successively for three days, the symptoms of the patient relieved significantly and the pH value of the vaginal secretions decreased to 4.0. The Gram smears showed a lot of Gram-positive bacilli, a few Gram-negative bacilli, but also an increased number of yeast-like organisms. Thus the treatment was stopped. Three days later after stopping the treatment, the patient's vaginal pH value increased to 4.4, Gram-stained vaginal smear showed there were lots of Gram-negative bacilli again as well as some yeast-like organisms in her vaginal smear. Then the patient was treated with the composition of Formulation Example 1 of this invention, 2 ml each time, once a day, for three days. The symptoms of the patient were gone and the pH value of the vaginal secretion was 4.0 after the treatment. Checking the patient's vaginal flora again and found there were a lot of Gram-positive bacilli and few Gram-negative bacilli on the Gram-stained vaginal smears, no yeast-like organisms were found. This case showed that the combination use of sucrose and Fluconazole could promote the growth of Gram-positive-bacilli while preventing the adverse growth of vaginal yeast-like organisms.

Reference:
1) German-M, et al: Genital flora in pregnancy and its association with intrauterine growth retardation. J-Clin-Microbiol. 1994 Sep: 32(9): 2162–8.
2) McDonald-HM, et al: Vaginal infection and preterm labour. Br-J-Obstet-Gynaecol. 1991 May; 98(5): 427–35.
3) Eschenbach. D A, Clin.Infect.Dis. 1993.1 6(Suppl.4): 5282–7.
4) Thomason J L. Bacterial vaginosis: current review with indications for asymptomatic therapy. Am J Obstet Gynecol .1991; 165: 1210.
5) Stein-GE, et al: Placebo-controlled trial of intravaginal clindamycin 2% cream for the treatment of bacterial. vaginosis. Ann-Pharmacother. 1993 Nov, 27(11): 1343–5.
6) Hillier-S L, et al: Efficacy of intravaginal 0.75% metronidazole gel for the treatment of bacterial vaginosis . Obstet-Gynecol. 1993 Jun; 81(6): 963–7.
7) Hoster-E, et al: Treatment of bacterial vaginosis in pregnancy with a lactate gel. Scand-J-Infect-Dis. 1990; 22(5):625–6.
8) Boeke-A J, et al: Effect of lactic acid suppositories compared with oral metronidazole and placebo in bacterial vaginosis: a randomised clinical trial. Genitourrin-Med. 1993 Oct; 69(5): 388–92.
9) Hallen-A, et al: Treatment of bacterial vaginosis with lactobacilli. Sex-Transm-Dis. 1992 May-Jun; 19(3): 146–8.
10) Hughes-V L, et al: Microbiologic characteristics of lactobacillus products used for colonization of the vagina. Obstet-Gynecol. 1990 Feb; 75(2): 244–8.

I claim:

1. A method for treating a patient suffering from vaginitis, a disturbance of the vaginal bacterial flora or bacterial vaginosis, wherein said vaginitis, disturbance of the vaginal bacterial flora or bacterial vaginosis are accompanied with a reduction of the number of Gram-positive bacilli, said method comprising vaginally administering to a subject in need of such treatment a therapeutically effective amount of a composition comprising:
   a) sucrose and/or maltose in a concentration of from about 2.5% to about 17% w/v based on the total volume of the composition,
   b) anti-fungal drug in a concentration of from about 0.0001% to about 5% w/v based on the total volume of the composition, and
   c) a sufficient amount of a pharmaceutically acceptable acid or alkali, which results in a pH of the composition from about 4.1 to about 7.2;
   wherein said administration promotes selective growth of gram-positive bacilli in the vagina of said subject.

2. A method for treating a patient suffering from vaginitis, a disturbance of the vaginal bacterial flora or bacterial vaginosis, wherein said vaginitis, disturbance of the vaginal bacterial flora or bacterial vaginosis are accompanied with a reduction of the number of Gram-positive bacilli, said method comprising, simultaneously or sequentially, vaginally administering to a subject in need of such treatment a therapeutically effective amount of a composition (A) and composition (B), wherein composition (A) comprises:

a) sucrose and/or maltose in a concentration of from about 2.5% to about 17% w/v based on the total volume of the composition, and b) a sufficient amount of a pharmaceutically acceptable acid or alkali, which results in a pH of the composition from about 4.1 to about 7.2; and composition (B) comprises:

(a) anti-fungal drug in a concentration of from about 0.0001% to about 5% w/v based on the total volume of the composition, and (b) a sufficient amount of a pharmaceutically acceptable acid or alkali, which results in a pH of the composition from about 4.1 to about 7.2.

3. The method according to claim 2, wherein composition (A) and composition (B) are vaginally administering to a subject in need of such treatment simultaneously.

4. The method according to claim 1, wherein said composition further comprising one or more saccharides selected from the group consisting of glucose, fructose, galactose, mannose, lactose, lactulose, mycose, cellobiose, melibiose, malto-oligosaccharide, iso-malto-oligosaccharide and oligo-fructose, dextrin, starch and glycogen.

5. The method according to claim 1, wherein the content of sucrose and/or maltose in said composition is from about 8% to about 14% w/v.

6. The method according to claim 1, wherein the content of anti-fungal drug in said composition is from about 0.001% to about 0.5% w/v.

7. The method according to claim 1, wherein the anti-fungal drug is selected from the group consisting of Fluconazole, Terconazole, Tioconazole, Butoconazole, Ketoconazole, Itraconazole, Econazole, Miconazole and Cannitracin.

8. The method according to claim 7, wherein the anti-fungal drug is selected from the group consisting of Fluconazole, Terconazole and Tioconazole.

9. The method according to claim 1, wherein the composition is in the form of hydro-gel or ointment, or in the form of liquid for preparing intravaginal tampon.

10. The method according to claim 9, wherein the composition is in the form of hydro-gel or ointment and it comprises a pharmaceutically acceptable viscous base.

11. The method according claim 10, wherein the pharmaceutically acceptable viscous base is Xanthan gum.

12. The method according to claim 2, wherein said composition (A) further comprises one or more saccharides selected from the group consisting of glucose, fructose, galactose, mannose, lactose, lactulose, mycose, cellobiose, melibiose, melitose, malto-oligosaccharide, iso-malto-oligosaccharide and oligo-fructose, dextrin, starch and glycogen.

13. The method according to claim 2, wherein the content of sucrose and/or maltose in said composition (A) is from about 8% to about 14% w/v.

14. The method according to claim 2, wherein the content of anti-fungal drug in said composition (B) is from about 0.001% to about 0.5% w/v.

15. The method according to claim 2, wherein the anti-fungal drug in said composition (B) is selected from the group consisting of Fluconazole, Terconazole, Tioconazole, Butoconazole, Ketoconazole, Itraconazole, Econazole, Miconazole and Cannitracin.

16. The method according to claim 15, wherein the anti-fungal drug is selected from the group consisting of Fluconazole, Terconazole and Tioconazole.

17. The method according to claim 2, wherein the compositions are in the form of hydro-gel or ointment, or in the form of liquid for preparing intravaginal tampon.

18. The method according to claim 17, wherein the compositions are in the form of hydro-gel or ointment and it comprises a pharmaceutically acceptable viscous base.

19. The method according to claim 18, wherein the pharmaceutically acceptable viscous base is Xanthan gum.

* * * * *